US009421281B2

(12) United States Patent
Texier-Nogues et al.

(10) Patent No.: US 9,421,281 B2
(45) Date of Patent: Aug. 23, 2016

(54) TARGET VECTOR WITH ACTIVABLE IMAGING FUNCTION

(75) Inventors: Isabelle Texier-Nogues, Grenoble (FR); Jean-Luc Coll, Claix (FR); Pascal Dumy, Allevard (FR); Didier Boturyn, Grenoble (FR); Marie Favrot, Corenc (FR)

(73) Assignees: Centre National de la Recherche Scientifique, Paris (FR); Commissariat a l'Energie Atomique et aux Energies Alternatives, Paris (FR); Institut National de la Sante et de la Recherche Medicale (INSERM), Paris (FR); The Joseph Fourier University of Grenoble, Grenoble (FR)

( * ) Notice: Subject to any disclaimer, the term of this patent is extended or adjusted under 35 U.S.C. 154(b) by 1355 days.

(21) Appl. No.: 11/996,208

(22) PCT Filed: Jul. 18, 2006

(86) PCT No.: PCT/FR2006/001749
§ 371 (c)(1),
(2), (4) Date: Jul. 18, 2008

(87) PCT Pub. No.: WO2007/010128
PCT Pub. Date: Jan. 25, 2007

(65) Prior Publication Data
US 2008/0292556 A1 Nov. 27, 2008

(30) Foreign Application Priority Data
Jul. 21, 2005 (FR) ...................................... 05 07784

(51) Int. Cl.
*A61K 49/00* (2006.01)
*A61K 47/48* (2006.01)

(52) U.S. Cl.
CPC ..... *A61K 49/0056* (2013.01); *A61K 47/48238* (2013.01); *A61K 49/0002* (2013.01); *A61K 49/0032* (2013.01); *A61K 49/0041* (2013.01); *A61K 49/0052* (2013.01)

(58) Field of Classification Search
CPC .................. A61K 49/0056; A61K 47/48238; A61K 49/0002; A61K 49/0041; A61K 49/0052
See application file for complete search history.

(56) References Cited

U.S. PATENT DOCUMENTS

2005/0142068 A1 6/2005 Verdugo-Gazdik

FOREIGN PATENT DOCUMENTS

WO 02 00265 1/2002
WO 2004 026894 4/2004

OTHER PUBLICATIONS

Hallbrink et al., Cargo delivery kinetics of cell-penetrating peptides, Biochim Biophys Acta. 1515(2):101-9, 2001.*
Texier et al., Luminescent probes for optical in vivo imaging, Proc. SPIE, vol. 5704:16-23, 2005.*
Tung et al., Fluorescent peptide probes for in vivo diagnostic imaging, Biopolymers 76(5):391-403, 2004.*
Heberle et al., Fluorescence methods to detect phase boundaries in lipid bilayer mixtures, Biochim Biophys Acta. 1746(3):186-92, 2005.*
Jiang et al., Tumor imaging by means of proteolytic activation of cell-penetrating peptides, Proc Natl Acad Sci U S A. 101(51):17867-72, 2004.*
Xing et al, J Am Chem Soc, Mar. 3, 2005, 127:4158-4159.*
Fichna et al, Bioconjugate Chem, 2003, 14:3-17.*
Gadella et al, J Cell Biol, 1995, 129:1543-15458.*
Choi et al, University of Cambridge Summer Meeting, Jul. 2005, vol. 3, Issue2, Abstract 010P.*
Damjanovich, Biophysical Aspects of Transmembrane Signaling— Springer Science and Business Media, Mar. 30, 2006, p. 53.*
Josephson, Lee et al., "Near-Infrared Fluorescent Nanoparticles as Combined MR/Optical Imaging Probes", Bioconjugate Chemistry, vol. 13, No. 3, pp. 554 to 560, 2002.
Curnis, Flavio et al., "Differential Binding of Drugs Containing the NGR Motif to CD13 Isoforms in Tumor Vessels, Epithelia, and Myeloid Cells", Cancer Research, vol. 62, pp. 867 to 874, 2002.
Van Hensbergen, Yvette et al., "A Doxorabicin-CNGRC-Peptide Conjugate With Prodrug Properties", Biochemical Pharmacology, vol. 63, No. 5, pp. 897 to 908, 2002.
Boturyn, Didier et al., "Template Assembled Cyclopeptides as Multimeric System for Integrin Targeting and Endocytosis", Journal of the American Chemistry Society, vol. 126, No. 18, pp. 5730 to 5739, 2004.
Garanger, Elisabeth et al., "New Multifunctional Molecular Conjugate Vector for Targeting Imaging, and Therapy of Tumors", Molecular Therapy, vol. 12, No. 6, pp. 1168 to 1175, 2005.
Law, Benedict et al., "Design, Synthesis and Characterization of Urokinase Plasminogen-Activator-Sensitive Near-Infrared Reporter", Chemistry and Biology, vol. 11, No. 1, pp. 99 to 106, 2004.
Chen, Xiaoyuan et al., "In Vivo Near-Infrared Fluorescence Imaging of Integrin αvβ3 in Brain Tumor Xenografts", Cancer Research, vol. 64, No. 21, pp. 8009 to 8014, 2004.
Arap, Wadih et al., "Cancer Treatment by Targeted Drug Delivery to Tumor Vasculature in a Mouse Model", Science, vol. 279, pp. 377 to 380, 1998.

* cited by examiner

*Primary Examiner* — Thaian N Ton
(74) *Attorney, Agent, or Firm* — Morgan, Lewis & Bockius LLP

(57) ABSTRACT

The invention concerns the field of molecular probe architecture for in vivo imaging. More particularly, the invention concerns molecular constructs providing an imaging function activable in intracellular environment. The inventive fluorescence probes enable in particular images of certain targeted tissues to be formed, while maintaining a low background noise level and, preferably, while obtaining at the targeted tissue, an imaging signal increasing in time.

14 Claims, 15 Drawing Sheets

A

B

TARGET VECTOR WITH ACTIVABLE IMAGING FUNCTION

The present invention relates to the field of the architecture of molecular probes for in vivo imaging. More particularly, the invention relates to molecular constructs providing a fluorescence imaging function activatable in an intracellular medium, these constructs also being bound to a vector which allows the targeting thereof to certain cells, and internalization in the cells in question.

The recent development of optical methods for fluorescence imaging in vivo in small animals opens up new horizons for functional imaging. It is now possible to follow, in real time and noninvasively, what becomes of luminescent molecules, and their biodistribution, and to establish a diagnosis and evaluate the effect of a therapy by virtue of these molecules. The advantages of optical imaging compared with the other functional imaging techniques (MRI, PET, SPECT) are the following:
- no handling of radioactive molecules and the constraints which are associated therewith (radioprotection, waste management, synchrotron source for PET labels),
- low cost of instrumentation,
- good sensitivity compared with magnetic resonance imaging (MRI) in terms of amount of label injected.

Currently, functional optical imaging is essentially carried out using luminescent labels grafted to a biological ligand which makes it possible to target certain regions of the individual (organs, cells, tumors, etc.).

Various luminescent labels have been developed for this type of imaging. Firstly, mention may be made of probes based on organic fluorophores. The first label used, ICG (Indo Cyanin Green), was, very early on, used "naked" (injection of the fluorophore alone), for imaging/visualizing vascularization and circulation in the blood vessels; these organic fluorophores have subsequently been grafted onto proteins or antibodies for targeting various cells (Folli, Westerman et al. 1994; Neri, Carnemolla et al. 1997; Ballou, Fisher et al. 1995; Ballou, Fisher et al. 1998; Becker, Riefke et al. 2000). However, coupling to these large molecules has drawbacks with respect to targeting and pharmacokinetics (Bugaj, Achilefu et al. 2001); consequently, the functionalization of fluorophores with small peptides has recently been preferred (Achilefu, Dorshow et al. 2000; Bugaj, Achilefu et al. 2001; Licha, Hessenius et al. 2001; Becker, Hessenius et al. 2001).

A second type of label for in vivo fluorescence imaging is the class of probes based on luminescent semiconductor nanocrystals (Michalet, Pinaud et al. 2005). The major drawback of these labels is their poor pharmacokinetics, which necessitate a special chemical coating (Ballou, Lagerholm et al. 2004; Gao, Cui et al. 2004). A single publication has up until now been published regarding such functionalized luminescent labels for targeting tumors (Gao, Cui et al. 2004).

However, the labels presented above exhibit a major limitation related to the nonspecific signal originating from the nontargeted parts of the individual's body. In fact, the existing biological ligands do not allow 100% targeting, and the targeting kinetics may be slow. Furthermore, during this period of time in which the probe binds to its receptor, said probe is already beginning to be metabolized by the organism. Under these conditions, the optimal time period for observation of the targeted biological process, i.e. the time period during which the region of interest/rest of the animal's body contrast is greatest, may be short and difficult to determine. In addition, the region of interest/rest of the individual's body contrast that is obtained remains low. This problem is even more essential for fluorescence imaging than for the other imaging techniques, since the very high degree of light scattering in the tissues means that the level of the nonspecific signal is very high. This thus makes any tomographical method for locating the probes difficult to implement.

In order to improve the targeting, certain teams have proposed, rather than simply grafting the luminescent label to a biological ligand for targeting the region to be imaged, using more complex vectors. Thus, the use of nanoparticles, such as polymer nanoparticles (Weissleder, Tung et al. 1999; Bremer, Tung et al. 2001) or semiconductor nanocrystals (therefore playing both the role of vector and the role of luminescent label (Michalet, Pinaud et al. 2005)), is beginning to be widespread. Nevertheless, the grafting of various entities onto these nanoparticles is complex; thus, only the functionalization of luminescent semiconductor nanocrystals with a targeting entity (Gao, Cui et al. 2004) and the functionalization of polymer particles with an imaging function (Weissleder, Tung et al. 1999; Bremer, Tung et al. 2001) have been proposed.

Recently, two molecular assemblies, capable of constituting alternatives to nanoparticles for carrying targeting functions and a label for fluorescence imaging, have been described (Boturyn, Coll et al. 2004; Dumy, Favrot et al. 2004; Maison, Frangioni et al. 2004). The first, called RAFT (*Regioselectively Addressable Functionalized Template*), is a cyclodecapeptide; the second is an adamantane derivative.

Another approach for reducing the background noise during the use of fluorescent probes consists in using probes that are specifically "activatable" in certain cells.

The principle of the first-generation activatable probes is to use a PEG/polylysine polymer as vector (Weissleder, Tung et al. 1999). A Cy5.5 fluorophore is bound to the polymer backbone via a pendent arm. The ratio of the number of fluorophores per unit of polymer is optimized such that the Cy5.5s are sufficiently close for their fluorescence to be self-quenched, and for the probe to be initially very weakly fluorescent. Certain enzymes, in particular overexpressed in certain tumor models, are capable of cleaving the polymer backbone. Under the action of these enzymes, the fluorophores are therefore separated and capable of emitting. For example, Weissleder et al. measure, with this probe, a fluorescence signal 80 times higher in a tumor model than in the blood, although the concentration of probes therein is 10 times lower (Weissleder, Tung et al. 1999).

The second generation of activatable probes adapts the principle for specific imaging of a proteolytic enzymatic activity (i.e. capable of cleaving a protein) (Bremer, Tung et al. 2001). This time, the pendent arm between the polymeric backbone and the fluorophore is a peptide arm, specific for the enzymatic activity to be imaged. Thus, the peptide used will vary according to whether it is desired to image MMP2 activity (Bremer, Tung et al. 2001), cathepsin D activity (Tung, Bredow et al. 1999; Tung, Mahmood et al. 2000) or thrombin activation in the blood (Tung, Gerszten et al. 2002).

More recently, this group has used the principle, no longer of self-quenching of the fluorescence of the same fluorophore, but of quenching of the fluorescence of a fluorophore by another quencher (Pham, Choi et al. 2005). These photophysical and photochemical processes are well known to those skilled in the art and are described, for example, in the work by J. Lakowicz (Lakowicz 1999). They are used for imaging an enzymatic activity: after enzymatic cleavage of the peptide arm, the fluorophore and its quencher are separated and the fluorophore can then emit (Pham, Choi et al. 2005).

The probes proposed in these studies are therefore probes which are initially nonfluorescent, and the fluorescence of which is triggered only in the areas where there exists the enzymatic activity to be imaged and for just such a purpose the probes were structured. However, these probes have the following drawbacks:

- they are limited to imaging an enzymatic activity, and the principle used cannot be broadened for detecting other biological processes, such as the recognition of a receptor by a ligand,
- an enzymatically cleavable peptide arm must be determined for each enzyme whose activity it is desired to image,
- these probes do not, a priori, go to localized regions of the animal, and thus can result in an unwanted signal. For example, the probes for imaging the enzymatic activity of MMP2 or of cathepsin D have been used to image tumors overexpressing these enzymes. However, the peptide arm of these probes can be cleaved by other proteases. In addition, in the absence of targeting, the amount of probes to be used is considerable.

There exists, therefore, at this time a real need for a targeted imaging vector which is such that the background noise in the nontargeted regions is zero or virtually zero, and that the intensity of the emission signal, in the targeting region, is independent of a specific enzymatic activity (present only in certain cell types, or of varying level depending on the cells), in order to obtain an image that faithfully reflects the targeting itself. The aim of the present invention is to provide imaging tools that remedy at least some of the drawbacks of the current vectors, as disclosed above.

For this, the inventors have developed a molecular system which allows the activation of an imaging function in the intracellular medium of any eukaryotic cell. The coupling of such a system to a targeted vector which is internalized in the target cells enables the emission signal to be triggered only after a target cell has been attained.

A first subject of the invention is therefore a targeted biological vector having an imaging function activatable in the intracellular medium, and such that the imaging function is activated by an ubiquitous mechanism. The term "ubiquitous mechanism" is herein intended to mean a mechanism which occurs in the intracellular medium of any eukaryotic cell. In the following text, an "imaging function" will denote the function itself, but also, by misuse of language, the means (fluorophores, luminescent particles, etc.) for obtaining this function. Similarly, a "targeting function" can denote the means used for the targeting (ligands, antibodies, etc.). A targeted biological vector comprising an imaging function may also be called a "probe".

According to a preferred embodiment of the vector of the invention, the activatable imaging function is provided by a fluorophore F linked to a fluorescence quencher by an arm cleavable in the intracellular medium. The internalization of the vector, subsequent to its binding to the target cell, will bring about the cleavage of the arm linking the fluorescence quencher to the fluorophore, and therefore the activation of the fluorescence. FIG. 1 illustrates this embodiment of the invention. The probe according to the invention is represented therein by the formula "vector-R1-X—Y—R2", where "vector" denotes the targeted vector, R1 and R2 are groups each containing a fluorophore or a fluorescence quencher, and X—Y represents the bond cleavable in an intracellular medium. A group Z, symbolizing a drug (therapeutic molecule, for example) is, where appropriate, attached to Y and/or to R2. In addition, the groups R1 and R2 may comprise a chemical bonding group for the attachment of said fluorophore or fluorescence quencher to the vector or to the arm that is cleaved (or, optionally, to the drug Z), and, where appropriate, a chemical spacer which makes it possible to reduce the steric interactions between, firstly, the vector and/or the arm that is cleaved and, secondly, the fluorophore and/or the fluorescence quencher. In the remainder of the present text, the notations R1, R2, X, Y and Z keep this meaning.

By way of examples of fluorophores F that can be used, mention may be made of:

- an organic fluorophore: many fluorophores are commercially available from various suppliers (Sigma-Aldrich, Molecular Probes, FluoProbes, etc.). These fluorophores may, inter alia, be fluoresceins coumarins, bodipys, porphyrins, cyanines, rhodamines or oxazines. This list is not exhaustive.
- nanoparticles (semiconductor nanocrystals (quantum dots), gold nanoparticles, polymer-based nanoparticles, oxide nanoparticles, etc.) having emission properties. This list is not exhaustive.

These fluorophores may be bonded to the vector and/or to the cleavable arm in particular by amide, ester, thioether or thioester functions. As mentioned above, a spacer arm between the vector and/or the cleavable arm and the fluorophore may also be present, in particular for reducing any possible quenching of the fluorescence of the fluorophore by the vector and/or the cleavable arm.

By way of nonfluorescent fluorescence quenchers, mention may be made of:

- an organic molecule: Dabcyl and derivatives, the BHQ family (Black Hole Quencher), Biosearch Technologies), the QSY family (Molecular Probes), or the CyQ family (Amersham). This list is not exhaustive. Such molecules are commercially available from at least two suppliers: Biosearch Technologies and Molecular Probes, Amersham Biosciences;
- nanoparticles such as semiconductor nanocrystals (quantum dots), gold nanoparticles, polymer-based nanoparticles, oxide nanoparticles. This list is not exhaustive.

These fluorescence quenchers may be bonded to the vector and/or to the cleavable arm by amide, ester, thioether or thioester functions, or the like. A spacer arm between the vector and/or the cleavable arm and the fluorescence quencher may also be present.

Some nonlimiting examples of structures of fluorophores and of fluorescence quenchers are given in FIG. 3.

The arm linking the fluorescence quencher and the fluorophore is preferably cleavable in the intracellular medium of any cell. The cleavage of the X—Y bond may, for example, be an acid-based, redox or organometallic reaction, possibly catalyzed by an enzyme. According to a preferred embodiment of the invention, the arm cleavable in an intracellular medium comprises a disulfide bridge. An example of an arm that can be used comprises a disulfide bridge between two cysteines (X=Y=Cys, the bond between the two cysteines being an S—S bond and not a peptide bond, the X—Y bond then being referred to as Cys-S—S-Cys). Another example is an arm which simply consists of two sulfur atoms (X=Y=S). When the cleavable arm comprises a disulfide bridge, the cleavage is catalyzed enzymatically by thioredoxins, in the lysosomes and endosomes of the cells (Arunachalam, Phan et al. 2000). Thioredoxins are small proteins involved in intracellular redox regulation, and therefore in numerous fundamental processes (response to stress, apoptosis, etc.). They reduce all the disulfide bridges of proteins entering the cell, but, unlike proteases, do not destroy the peptide bond between amino acids. They are present in all cells of all organisms.

In the context of the present invention, a large variety of structures may be used to constitute the core of the vector. The term "core of the vector" is herein intended to mean the molecule or the particle to which the imaging and targeting functions are bound. By way of examples of structures that can be used for the core of the vector, mention may be made of:

an organic nanoparticle: synthetic polymer (polystyrene, latex), or natural polymer (polysaccharide, liposome, etc.), optionally coated with a shell, such as a layer of silica. This may also be a nanoparticle composed of molecules organized in micelles, such as phospholipids. These particles may optionally trap a gas or encapsulate another molecular entity, such as a drug, for example;

a metal nanoparticle: gold nanoparticle, silver nanoparticle, chromium nanoparticle, bimetallic particle, etc., optionally coated with a shell, such as a layer of silica, a layer of thiol molecules and/or a layer of polymer;

a silica nanoparticle or an oxide or silicate nanoparticle (for example, but in a nonlimiting manner, yttrium oxide nanoparticle, yttrium silicate nanoparticle, vanadium oxide nanoparticle, titanium dioxide nanoparticle, etc.), optionally coated with a shell, such as a layer of silica, a layer of silanes, a layer of polymer;

a semiconductor nanoparticle, optionally coated with a shell, such as a layer of silica, a layer of thiol molecules, a layer of polymer;

a molecular entity that can play the role of a platform, that can carry various functions, such as the RAFT molecule or the adamantane mentioned above, or else molecules such as cyclodextrins, calixarenes, dendrimers, etc.

According to a preferred embodiment of the vectors according to the invention, the targeting is provided by at least one biological ligand recognized by a receptor overexpressed at the surface of certain cells. The biological ligands for specifically targeting certain cells may be:

peptides, for example the RGD peptide, or their derivatives or their analogs (for example: the octeotrate peptide, an analog of somatostatin, an analog of bombesin, neurotensin, EGF, VIP, etc.);

proteins, antibodies, or their derivatives or their analogs;

sugars, in particular monosaccharides (for example: glucose, galactose, glucosamine or galactosamine), oligosaccharides, polysaccharides, or their derivatives or their analogs;

oligonucleotides, DNA, RNA, their derivatives or their analogs;

organic molecules (such as folate or pamidronate bisphosphonate);

organometallic complexes.

Their targeting activity is due to the molecular recognition of these ligands by receptors overexpressed at the surface of the cells of the region of interest.

Ligands that are particularly preferred for implementing the invention are, for example, peptides comprising the RGD motif, such as cyclo(RGDfK), cyclo(RGDyK) or cyclo(RGDfV). These peptides recognize the $\alpha_v\beta_3$ integrin which is overexpressed at the surface of tumor cells and of endothelial cells during tumor neoangiogenesis. The use of these ligands in the vectors according to the invention therefore makes it possible to image the tumors and their vascularization, and, where appropriate, to deliver a drug to this site. Another preferred ligand is, for example, a peptide comprising the NGR motif described by Curnis et al. (Curnis, Arrigoni et al. 2002), which also targets neovessels.

According to a specific embodiment of the invention, the vector may comprise one or more label(s) for an imaging method other than fluorescence imaging, either in addition to the latter or as a replacement for the latter. These labels may be grafted to the surface of the vector, or encapsulated inside if this is a vector of nanoparticulate type; alternatively, the core of the vector may itself be a contrast agent (for example, an iron oxide nanoparticle, as contrast agent for MRI). Such labels may be:

gadolinium chelates, iron oxide nanoparticles, or nanoparticles of other contrast agents for MRI, known to those skilled in the art;

radiolabeled molecules, for example radiolabeled with $^{99}$Tc, $^{111}$In, $^{18}$F, $^{11}$C or $^{15}$O, used as contrast agents for nuclear imaging and known to those skilled in the art.

According to a specific embodiment of the invention, the vector is also capable of delivering a drug Z. This drug may be attached to the vector or to the cleavable arm by various chemical groups (for example: acid, ester, thioether or thioester functions) optionally via a spacer arm. It may also be bound to the vector by a cleavable arm, such as the arms of X—Y described above, or by another arm that is chemically cleavable or cleavable by another process (activation by light, ultrasound, radiofrequency, etc.). It may also be encapsulated in the vector. When the drug is either linked to the vector by the same cleavable arm as that contained in the imaging function, or is itself labeled with the fluorophore or the quencher of fluorescence of the imaging function, the activation of the imaging function also indicates the delivery of the drug.

The term "drug" is herein intended to mean any molecule capable of having an effect on the cell into which it will be delivered. This effect is preferably therapeutic for the individual to whom it is administered. By way of examples of drugs Z that can be used in the context of the invention, mention may be made of:

a therapeutic molecule already identified as such (for example: taxol, doxorubicin, paclitaxel, etc.), a natural or synthetic DNA or oligonucleotide, for example an siRNA intended to inhibit the synthesis of a protein, a natural or synthetic peptide or protein (obtained according to the techniques of those skilled in the art, by enzymatic digestion or by solid-support synthesis, for example), a monosaccharide, oligosaccharide or polysaccharide, or derivatives and analogs.

According to a specific embodiment of the invention, the activatable imaging function is provided by a fluorophore F linked to a fluorescence quencher by an arm cleavable in the intracellular medium, such that, after cleavage of said cleavable arm, the quencher remains bound to the vector and the fluorophore remains bound to the drug Z. According to the notation used in FIG. 1 and explained above, this implies that the drug Z is bound to the group R2 and/or to Y.

Several configurations of this embodiment, or of the embodiment "vector-R1-X—Y—R2" in the absence of drug Z, can be envisioned and readily implemented by those skilled in the art, depending on the application chosen. These various configurations are illustrated in FIG. 1C, and are an integral part of the invention.

In the case illustrated in FIG. 1C.1, the fluorophore F is on the group R1, and R2 comprises a nonfluorescent quencher of the fluorescence of F (R2 may be limited to this quencher). After activation of the imaging function, fluorescent labeling of the vector is then obtained, which makes it possible to visualize the targeting of the probe and to follow the biodistribution of the vector itself.

FIG. 1C.2 illustrates the case where the fluorophore F is on the group R2, and where a nonfluorescent quencher of the fluorescence F is on R1. After activation of the imaging function, fluorescent labeling of the cleaved product R2-Y or R2-Y—Z or Y—R2-Z is then obtained, which makes it possible to visualize the targeting of the probe and to follow the biodistribution of the cleaved product and therefore, where appropriate, of the drug Z delivered.

In the case where the same fluorophore F is on the group R1 and on the group R2, F should be a fluorophore whose fluorescence is capable of self-quenching. This is the case, for example, of the fluorophores of the cyanines family. The activation of the imaging function then makes it possible to visualize the targeting of the probe and to follow the vector and the cleaved product, without distinction. The fluorescence released is in this case potentially twice that released in the cases disclosed above and illustrated in FIGS. 1C.1 and 1C.2.

It is also possible to use a second fluorophore as fluorescence quencher. In this case, the two fluorophores F1 and F2 (with F1≠F2) are chosen such that the fluorophore F1, excited at its excitation wavelength $\lambda_{exc}$ (1), initially has its fluorescence quenched by the fluorophore F2 via the energy transfer process well known to those skilled in the art (Lakowicz 1999). There is then, initially, only an emission signal at the emission wavelength of F2, $\lambda_{em}$ (2), and not at the emission wavelength of F1, $\lambda_{em}$ (1) (FIG. 2). The activation of the imaging activity is reflected by the emission of a signal at the emission wavelength of F1, $\lambda_{em}$ (1) during excitation at $\lambda_{exc}$ (1).

In the case, illustrated in FIG. 1C.3, where the fluorophore F1 is on the group R1 and the fluorophore F2 is on the group R2, this signal indicates the targeting of the probe and makes it possible to visualize the biodistribution of the vector by exciting the system at the excitation wavelength of F1, $\lambda_{exc}$ (1), and detecting the signal at the emission wavelength of F1, $\lambda_{em}$ (1), and to visualize the biodistribution of the cleaved product by exciting the system at the excitation wavelength of F2, $\lambda_{exc}$ (2), and detecting the signal at the emission wavelength of F2, $\lambda_{em}$ (2) (FIG. 2). Excitation at the emission wavelength of F1, $\lambda_{exc}$ (1), and detection at $\lambda_{em}$ (2), also makes it possible to follow the biodistribution of the probe before activation of the imaging function (FIG. 2). Such a configuration therefore has the advantage of following both the biodistribution of the probe (by exciting at $\lambda_{exc}$ (2) and observing at $\lambda_{em}$ (2)), and the activation of the imaging function (by exciting at $\lambda_{exc}$ (1) and observing at $\lambda_{em}$ (1)) (FIG. 2). It is therefore one of the most advantageous configurations of the invention.

The roles of F1 and F2 may be reversed, i.e. F1 and F2 may be chosen such that the fluorophore F2, excited at its excitation wavelength $\lambda_{exc}$ (2), initially has its fluorescence quenched by the fluorophore F1. The activation of the imaging function will bring about the same result, i.e. visualizing the targeting of the probe and visualizing the biodistribution of the vector by exciting the system at the excitation wavelength of F1, $\lambda_{exc}$ (1), and detecting the signal at the emission wavelength of F1, $\lambda_{em}$ (1), and visualizing the biodistribution of the cleaved product by exciting the system at the excitation wavelength of F2, $\lambda_{exc}$ (2), and detecting the signal at the emission wavelength of F2, $\lambda_{em}$ (2).

The invention therefore also relates to the use of a vector as described above (configuration with two fluorophores F1 and F2), for delivering a drug, for example a therapeutic molecule, and simultaneously following the biodistribution of the vector and of the drug in question. This configuration, and also that in which R2 comprises a fluorophore F and R1 a pure fluorescence quencher, may also be used advantageously to follow, in real time, the biodistribution of a drug. The term "pure quencher" is herein intended to mean a fluorescence quencher which is itself nonfluorescent.

Preferably, a vector according to the present invention is electrically neutral before activation of the imaging function. This is because a neutral molecule penetrates more easily into the cell than a charged molecule. Thus, in the examples which follow, the vector RAFT-Cy5-Cys-S—S-Cys-Q penetrates into the cells better than the vector RAFT-Cy5-Cys-S—S-Cys-Cy5. It is, moreover, advantageous for the two molecules derived from the cleavage of the arm X—Y to be charged, since charged molecules remain more readily in the intracellular medium. Thus, in the example described later, the cleavage of the disulfide bridge of the vector RAFT-Cy5-Cys-S—S-Cys-Q (RAFT also being bound to a neutral ligand providing the targeting, and it being possible for the quencher Q to be coupled to an electrically neutral drug) gives two molecular entities of opposite charges.

According to a preferred embodiment of the vectors of the invention, the imaging function is therefore provided by a cyanines, for example the Cy5 fluorophore, linked by a disulfide bridge to a quencher of its fluorescence.

The results given in the experimental section below show that a vector according to the invention has pharmacokinetic properties such that the imaging response, in the region targeted, increases over time (FIG. 12), at least during the first hour following injection of the vector. This is at least in part related to the fact that the activation of the fluorescence takes place in the intracellular medium, and therefore only after the vector has reached a target cell and has been internalized. The use of a disulfide bridge, such that cleavage of the S—S bond results in activation of the imaging function, allows good signal appearance kinetics. FIGS. 5, 6, 10 and 11 show that the kinetics of chemical cleavage of the disulfide bridge by 2-mercaptoethanol (2-MCE) is slow, despite the high concentration of 2-MCE. The cleavage is even slower in the cell, since the concentration of enzyme is low. This results in a slow increase in the intensity of the signal, which remains for a long time and allows elimination of the nontargeted probe during this time, which favors specificity. This property of the vectors of the invention is particularly advantageous, since it gives the practitioner greater freedom of maneuver for acquiring the image—specific for the targeted region—under good conditions. This property of the vectors described herein is therefore an important aspect of the invention.

The examples given below in a nonlimiting manner will make it possible to demonstrate certain advantages and characteristics, and also other advantageous arrangements, of the present invention.

BRIEF DESCRIPTION OF DRAWINGS

FIG. 1A describes the principle of the targeting of the region of the individual to be imaged by the subject of the invention. The targeting is obtained by functionalization of the vector with a biological ligand specific for the cells of the region to be targeted.

FIG. 1B describes the process resulting in the activation of the imaging function of the subject of the invention. After molecular recognition between the cells of the targeted region and the biological ligand carried by the vector, the probe is internalized into the cells. The internalization of the probe into the cells triggers the activation of the imaging function (i.e. the fluorescence).

FIG. 1C describes the imaging function. The latter comprises at least one fluorophore F (either on the group R1 or on the group R2), an arm X—Y enzymatically cleavable in an intracellular medium, and a fluorescence quencher (either on the group R1 or on the group R2). The latter may be either a nonfluorescent fluorescence quencher, or another fluorophore. In the latter case, it may be the same fluorophore as F (if F is a self-quenching fluorophore), or another fluorophore that can absorb the radiation emitted by F and reemit it at another wavelength. This imaging function may also comprise another functionality, such as the presence of a drug Z, preferably grafted onto the cleavable part of the probe (i.e. Y—R2). In the intracellular medium, the cleavable arm X—Y is cleaved, separating the vector bound to the group R1-X, from the product R2-Y (or R2-Y—Z or Y—R2-Z).

EXAMPLES

Example 1

One Embodiment of the Invention

The embodiment of the invention described below is based on the use:
 Of the RAFT molecular vector previously described (Boturyn, Coll et al. 2004; Dumy, Favrot et al. 2004). The use of the RAFT molecular vector provides the invention with specific advantages which are the following:
  its molecular structure is precisely defined and well controlled, unlike a polymeric probe for which only the average molecular weight is determined;
  the molecular probe obtained can be readily purified according to techniques known to those skilled in the art (HPLC, for example), unlike a polymeric probe;
  this molecular probe is smaller in size than other nanoparticles, which promotes its internalization into the cells;
 Of the biological ligand cRGD previously described. The cRGD cyclopeptide was chosen as biological ligand since it has for a long time been known to target receptors of α$_v$β$_3$ integrins overexpressed at the surface of developing blood vessel endothelial cells (Brooks, Clark et al. 1994). These receptors are in particular overexpressed in various cancer cell models;
 Of the imaging functions Cy5-Cys-S—S-Cys-Cy5 and Cy5-Cys-S—S-Cys-QSY21 described below. These imaging functions use the disulfide bridge between two cysteines (cleavage catalyzed enzymatically by thioredoxins in the lysosomes and endosomes of the cells (Arunachalam, Phan et al. 2000)), the Cy5 fluorophore sold by Amersham and the QSY21 fluorescence quencher sold by Molecular Probes.

Cysteine (Cy5)-S—S-Cysteine (Cy5) Imaging Function

Figure 1:
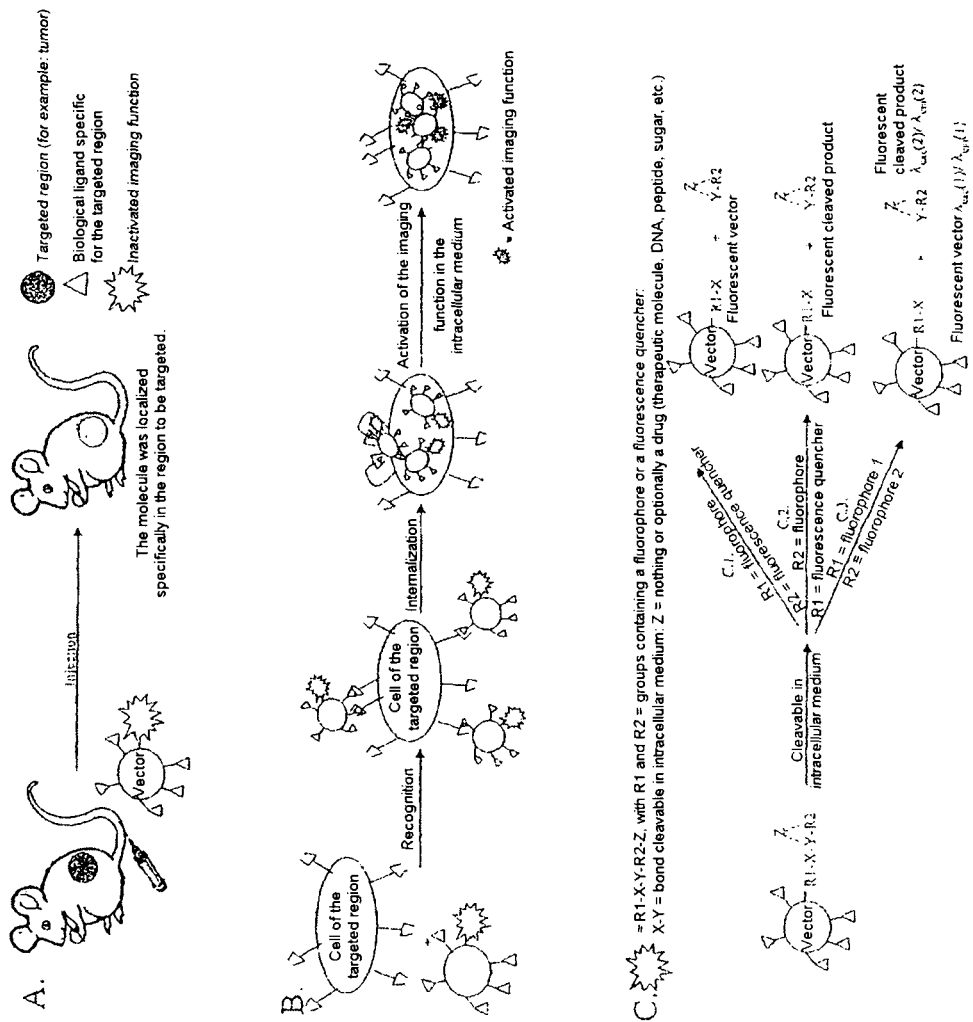
FIG. 1: this figure describes the principle of the invention. The probe initially comprises at least one biological ligand for the targeting (it may also comprise several thereof), and an inactivated imaging function. It may also comprise a drug-delivery function.
Figure 2:
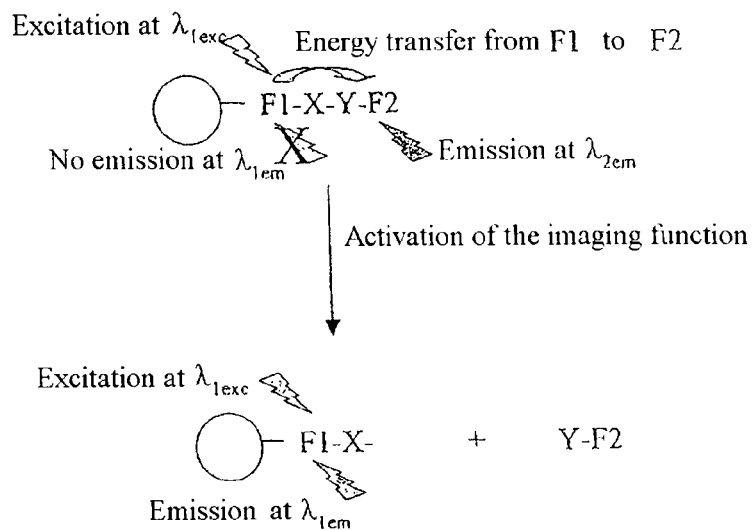
FIG. 2: The case where the fluorophore F1 is on the group R1 and the fluorophore F2 is on the group R2, F1≠F2, F1 and F2 chosen such that the fluorophore F, excited at its excitation wavelength $\lambda_{exc}$ (1), initially has its fluorescence quenched by the fluorophore F2 via the energy transfer process well known to those skilled in the art (Lakowicz 1999). There is then initially only an emission signal at the emission wavelength of F2, $\lambda_{em}$ (2), and not at the emission wavelength of F1, $\lambda_{em}$ (1). The activation of the imaging activity is reflected by the emission of a single at the emission wavelength of F1, $\lambda_{em}$ (1). This signal indicates the targeting of the probe and makes it possible to visualize the biodistribution of the vector by exciting the system at the excitation wavelength of F1, $\lambda_{exc}$ (1), and detecting the signal at the emission wavelength of F1, $\lambda_{em}$ (1), and to visualize the biodistribution of the cleaved product by exciting the system at the excitation wavelength of F2, $\lambda_{exc}$ (2), and detecting the signal at the emission wavelength of F2, $\lambda_{em}$ (2).
Figure 2:
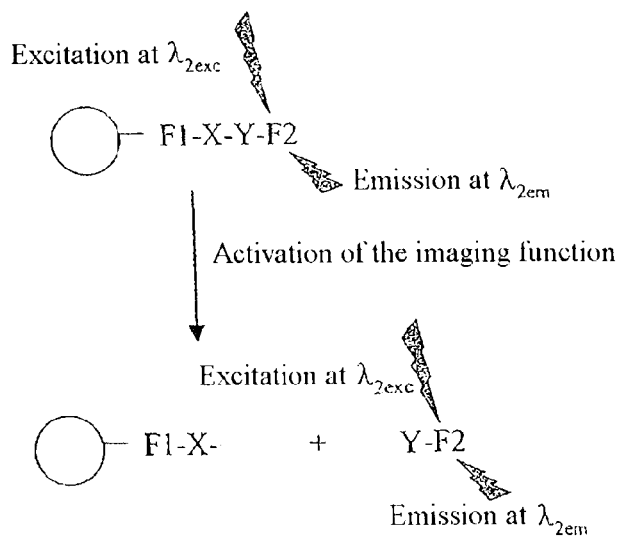
Figure 3:
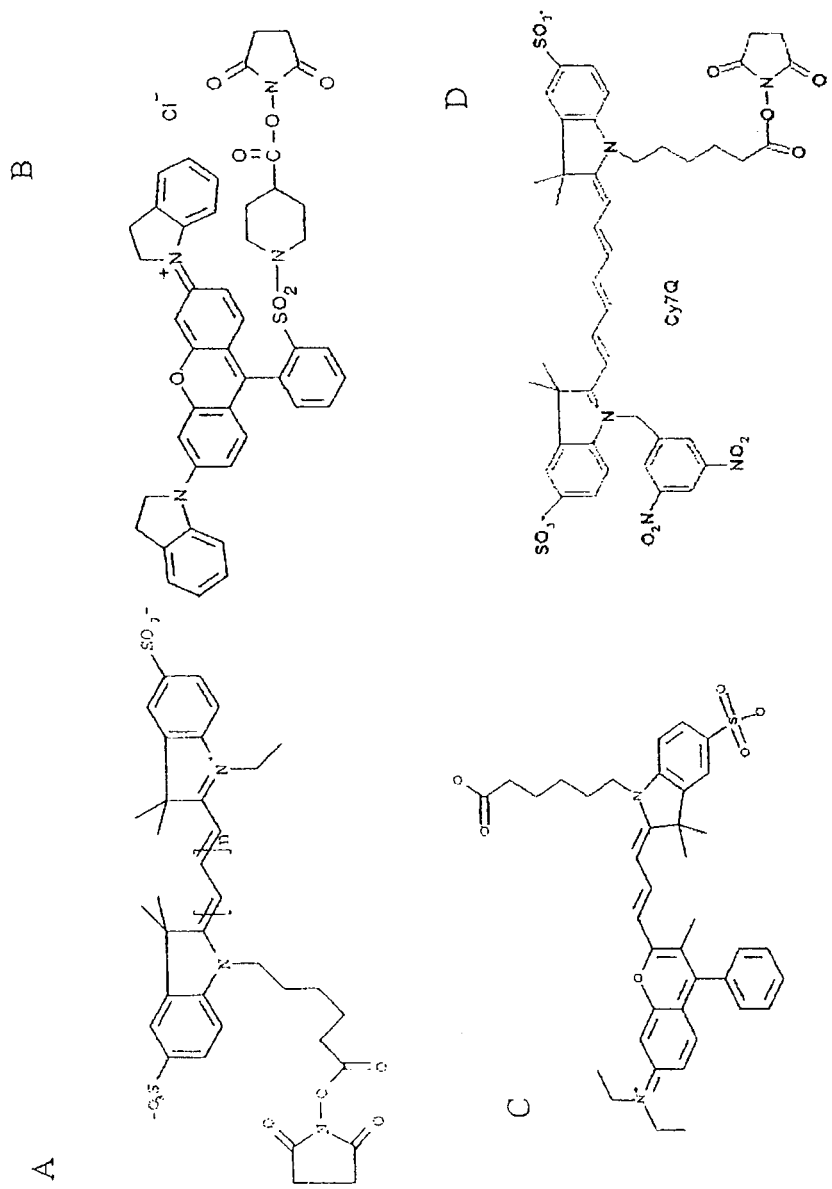
FIG. 3: Structure of some commercially available fluorophores and quenchers that can be used to prepare the subject of the invention. A: fluorophore: Cy5 (n=2) or Cy7 (n=3) N-hydroxysuccinimidyl ester, Amersham. B: quencher: QSY™ 21 N-hydroxysuccinimidyl ester, Molecular Probes. C: fluorophore: NIR 700—carboxylic acid, Fluka. D: quencher: Cy7Q—N-hydroxysuccinimidyl ester, Amersham/GE Healthcare. This figure is not an exhaustive list of the compounds that can be used according to the invention.
Figure 4:
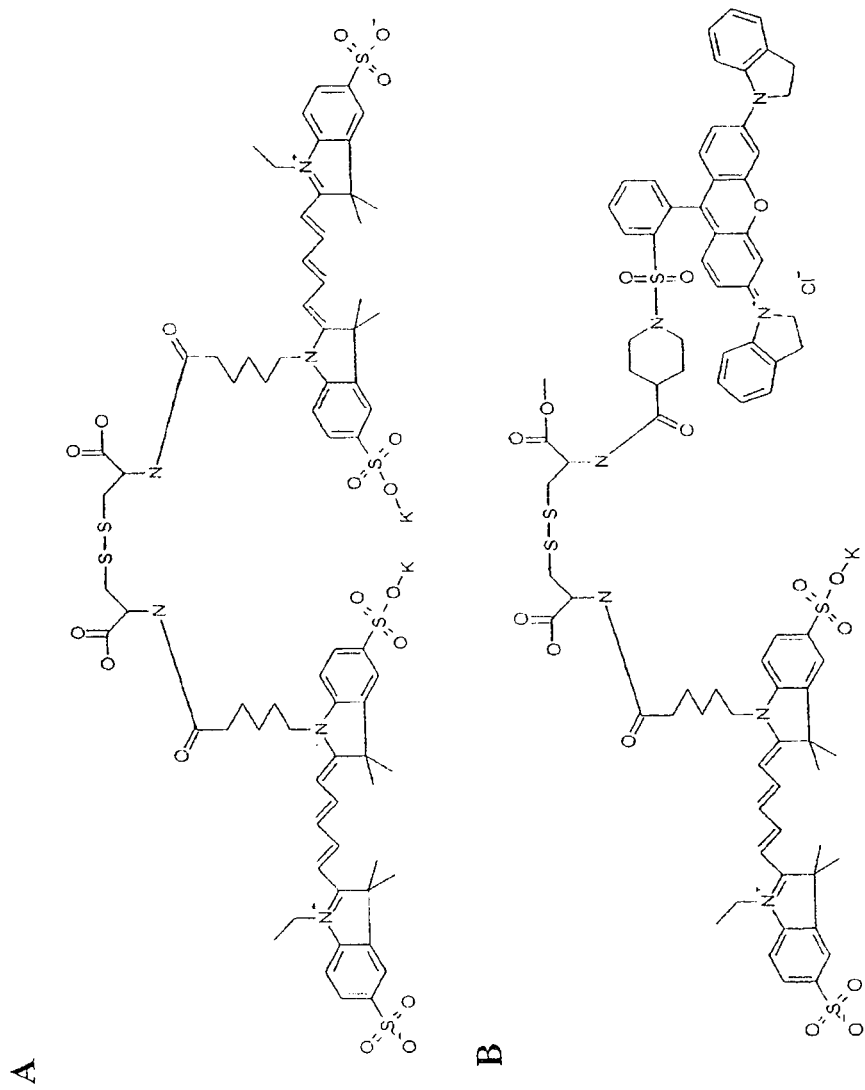
FIG. 4: Chemical structure of the imaging functions Cy5-Cys-S—S-Cys-Cy5 (A) and Cy5-Cys-S—S-Cys-QSY21 (B).
Figure 5:
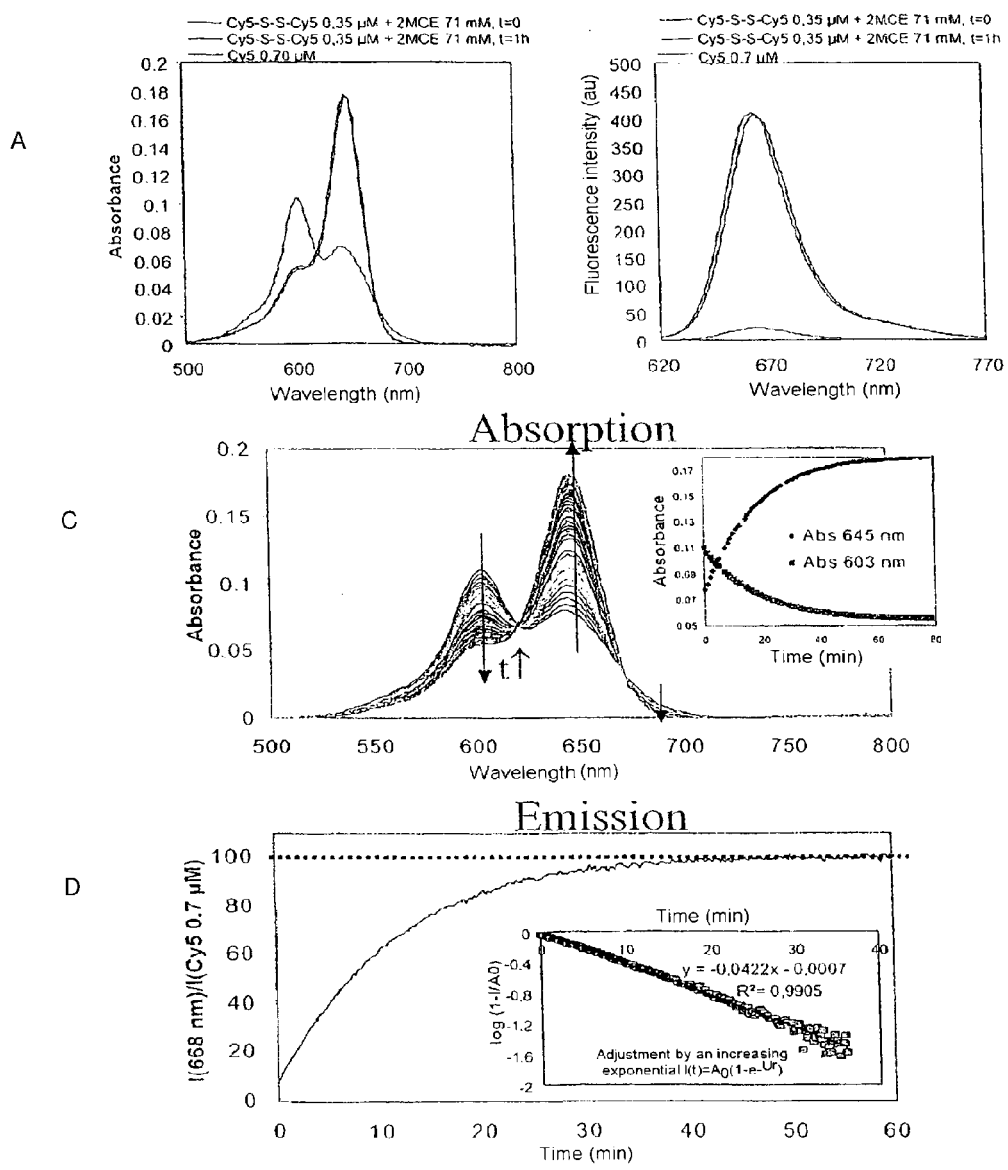
FIG. 5: Absorption and fluorescence of the imaging function Cy5-Cys-S—S-Cys-Cy5 before and after chemical cleavage of the disulfide bridge with 2-mercaptoethanol (2-MCE). A. Absorption spectrum and evolution thereof over time during the addition of 2-MCE. B. Demonstration that the addition of 2-MCE results in complete recovery of the absorption spectrum of Cy5. C. Evolution over time of the fluorescence of the imaging function during the addition of 2-MCE. D. Demonstration that the addition of 2-MCE results in complete recovery of the fluorescence of Cy5 (imaging function at 0.35 µM in 10 mM tris-HCl, pH 7.5, [2-MCE]=70 mM).

The chemical structure of this molecule is given in FIG. 4. It was prepared from cysteine (0.4 mg, 1.6 μmol) and from the activated N-hydroxysuccinimide ester of cyanine 5 (2.8 mg, 3.5 μmol) in a solution of DMF/H$_2$O (6:1) at pH 8.0. The product is obtained after purification by HPLC, in the form of a blue powder (1.2 mg, 0.8 μmol, 50%). FIG. 5 shows that the fluorescence of the Cy5 fluorophores is indeed initially self-quenched, and is completely released by chemical cleavage of the S—S disulfide bridge.

Cysteine (Cy5)-S—S-Cysteine (QSY21) Imaging Function

Figure 6:
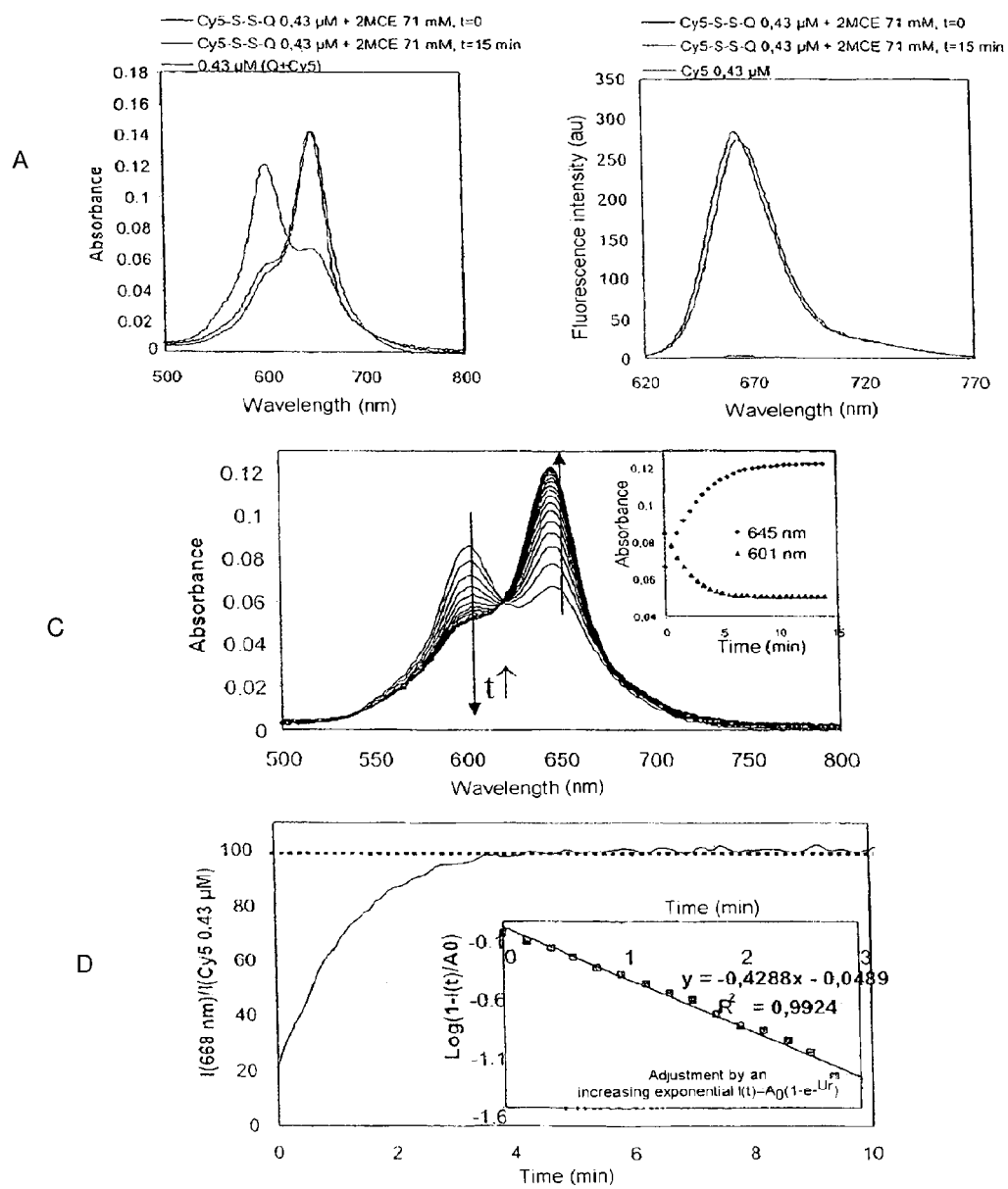
FIG. 6: Absorption and fluorescence of the imaging function Cy5-Cys-S—S-Cys-QSY21 before and after chemical cleavage of the disulfide bridge with 2-mercaptoethanol (2-MCE). A. Absorption spectra and evolution thereof over time during the addition of 2-MCE. B. Demonstration that the addition of 2-MCE results in complete recovery of the absorption spectrum of Cy5 and QSY21. C. Evolution over time of the fluorescence of the imaging function during the addition of 2-MCE. D. Demonstration that the addition of 2-MCE results in complete recovery of the fluorescence of Cy5 (imaging function at 0.35 µM in 10 mM tris-HCl, pH 7.5, [2-MCE]=70 mM).

The chemical structure of this molecule is given in FIG. 4. It was prepared from Boc-cysteine(Npys) (210 mg, 0.56 mmol). The Boc group is first of all eliminated in a solution of TFA/DCM (1:1) (138 mg, 0.5 mmol, 90%). Then, cyanine 5 N-hydroxysuccinimide (5 mg, 6.3 μmol) in a solution of DMF/H$_2$O (9:1), at pH 8.0 is added to a solution of cysteine (Npys) (1.7 mg, 6.3 μmol). After purification of the compound, cysteineOMe (6.1 mg, 6.1 μmol) is added and the pH is adjusted to 7.0 in water. Purification by HPLC gives the compound Cy5-Cys-SS-CysOMe in the form of a blue powder (2.4 mg, 2.5 μmol, 52%). This compound (2.4 mg, 2.5 μmol) is then taken up with QSY®21 succinimide ester (2 mg, 2.5 μmol) in DMF at pH 8.0. Purification by HPLC gives the desired product in the form of a blue powder (2.2 mg, 1.3 μmol, 54%). FIG. 6 shows that the fluorescence of the Cy5 fluorophore is indeed initially quenched by the QSY21, and is completely released by chemical cleavage of the S—S disulfide bridge.

Biological Validation of the Imaging Functions

Figure 7:
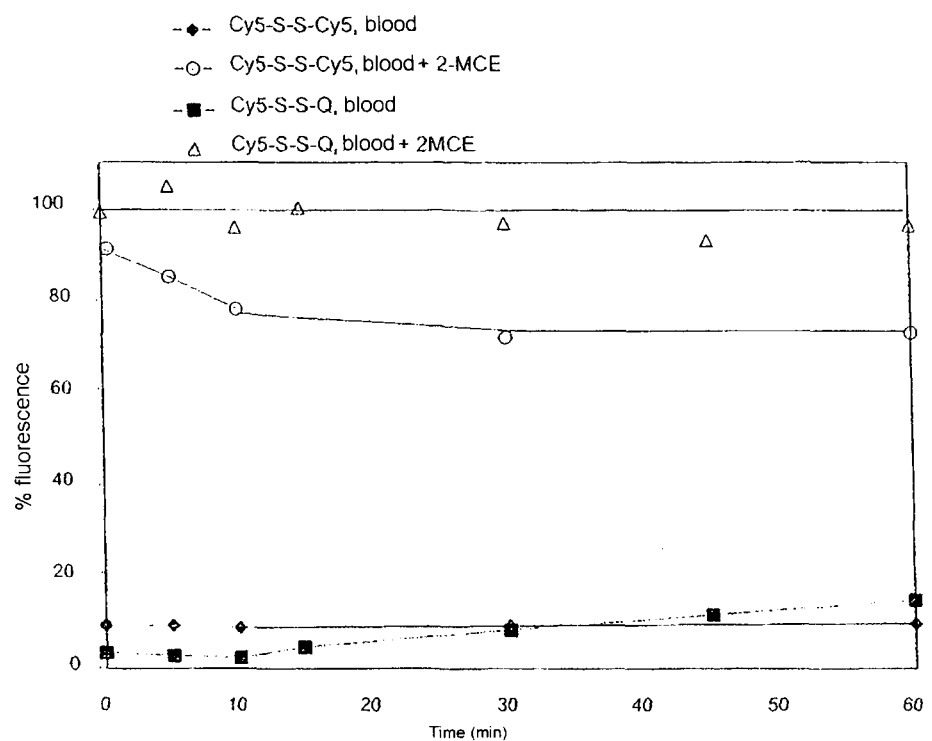
FIG. 7: Evolution of the fluorescence of the imaging functions Cy5-Cys-S—S-Cys-Cy5 and Cy5-Cys-S—S-Cys-QSY21≈0.4 µM, incubated in mouse blood. The solid symbols represent the fluorescence measured in the supernatant just after centrifugation of the samples taken after various incubation time periods. The open symbols represent the fluorescence measured on these same samples, 1 h after addition of 2-mercaptoethanol (70 mM). The latter curves therefore make it possible to evaluate the proportion of the imaging function adsorbed onto the blood proteins.

FIG. 7 shows that the fluorescence of the imaging functions is not released when they are circulating in the blood in mice. It also shows that no nonspecific adsorption of the Cy5-Cys-S—S-Cys-QSY21 imaging function occurs on the blood proteins, whereas 25% adsorption occurs for the Cy5-Cys-S—S-Cys-Cy5 function.

Figure 8:
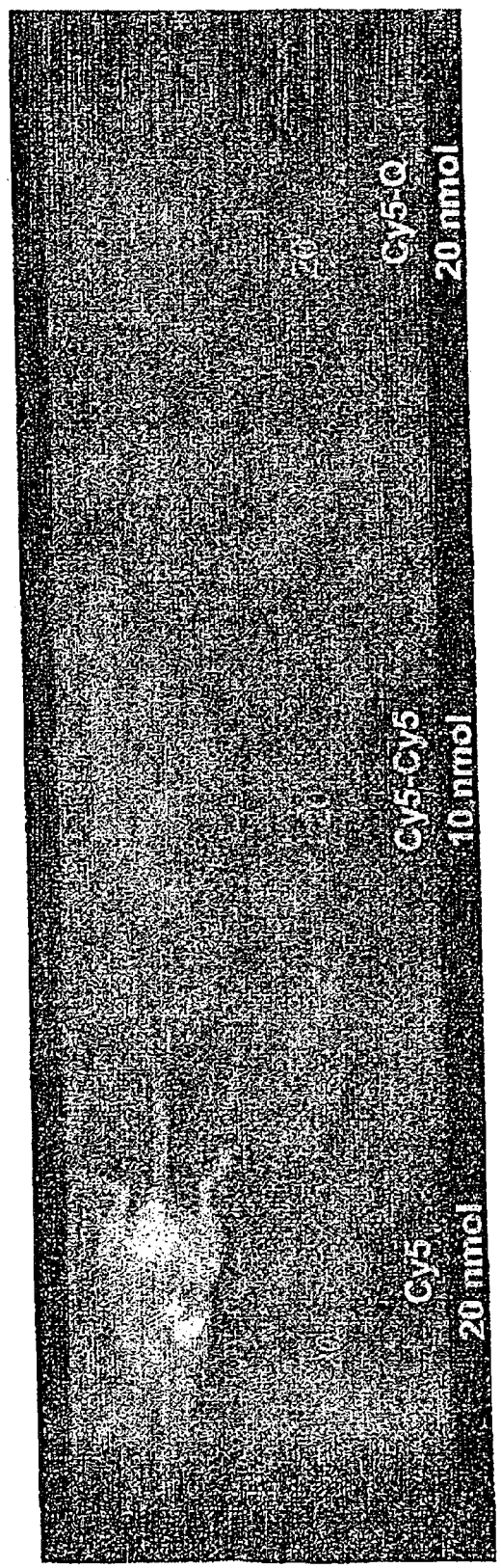
FIG. 8: Fluorescence of the imaging functions Cy5-Cys-S—S-Cys-Cy5 and Cy5-Cys-S—S-Cys-QSY21 20 minutes after intravenous injection into anesthetized nude mice. The image acquisition is carried out with a fluorescence reflectance imaging (FRI) device, comprising as excitation source a crown of LEDs equipped with interference filters, emitting at 633 nm (illumination power 50 µW·cm$^{-2}$). The images are collected after filtration by means of a colored filter RG665 of optical density>5 at the excitation wavelength by a CCD camera (Orca BTL, Hamamatsu) with an exposure time of 100 ms.

FIG. 8 confirms these results: after intravenous injection of the imaging functions, no fluorescence is observed, unlike the case of the nonfunctionalized Cy5 fluorophore.

Figure 9:
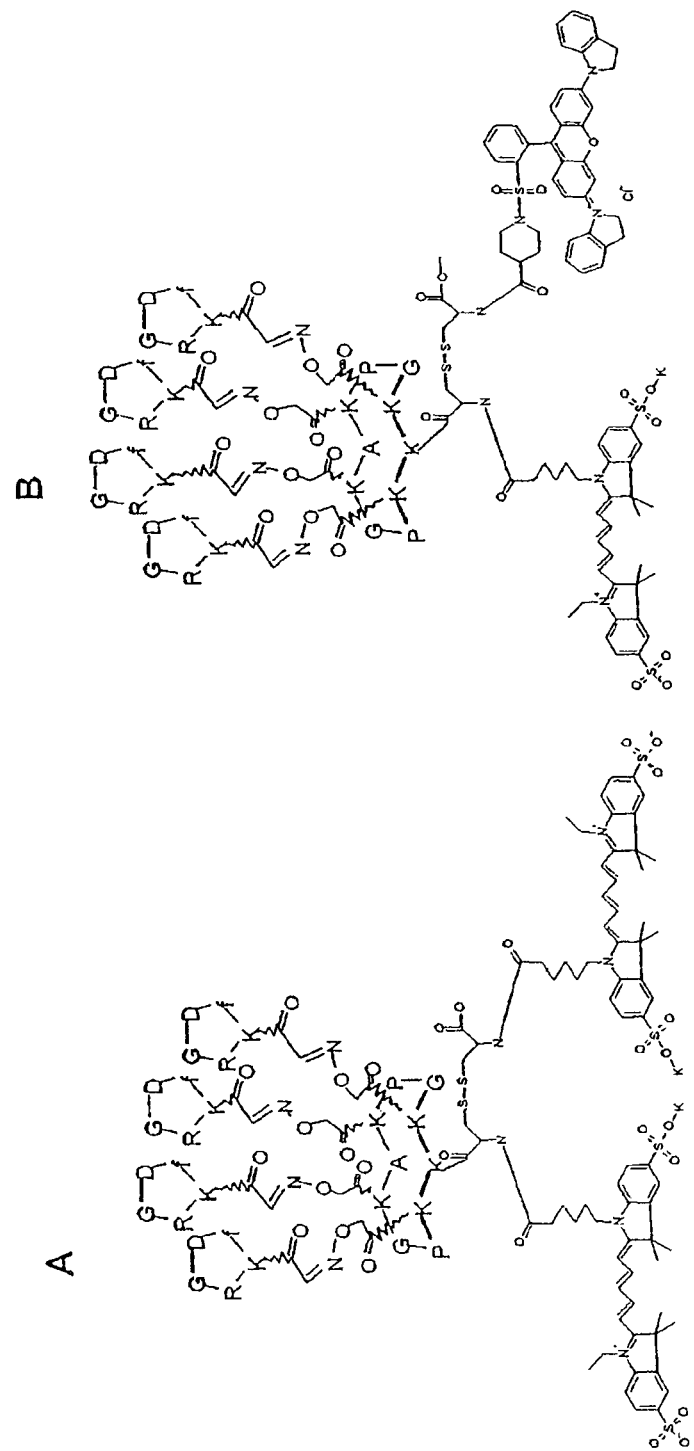
FIG. 9: Chemical structure of the RAFT-(cRGD)$_4$-F molecules where F represents the imaging functions Cy5-Cys-S—S-Cys-Cy5 (A) and Cy5-Cys-S—S-Cys-QSY21 (B).

Synthesis of the Molecular Probe Cysteine(Cy5)-S—S-Cysteine(Cy5) RAFTc[-RGDfK]$_4$ FIG. 9 gives the structure of the cysteine(Cy5)-S—S-cysteine(Cy5)RAFTc[RGDfK-]$_4$ molecule. The cysteine (Npys)RAFTc[-RGDfK]$_4$ peptide (10 mg, 2.26 μmol) is taken up in 0.5 ml of DMF/PBS, pH 4.8, 3/1 with cysteine (0.3 mg, 2.7 μmol). The product is purified by HPLC (5.3 mg, 53%). The cysteine-S—S-cysteineRAFTc[-RGDfK]$_4$ peptide (3.5 mg, 0.79 μmol) is taken up in 300 μl of DMF with cyanines 5 N-hydroxysuccinimide (1.9 mg, 2.4 μmol). The final product is purified by HPLC and obtained in the form of a blue powder (2.4 mg, 54%).

Figure 10:
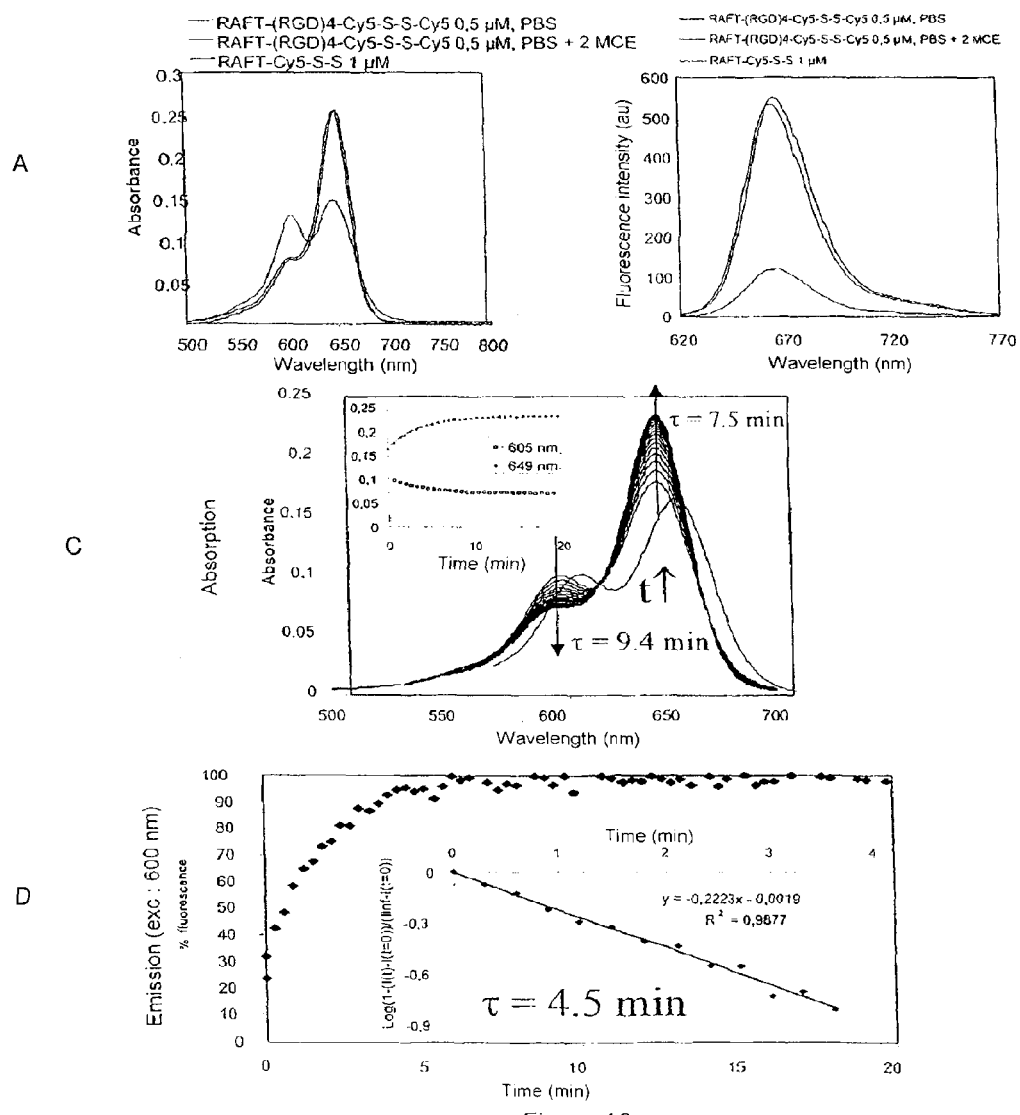
FIG. 10: Absorption and fluorescence of the imaging function Cy5-Cys-S—S-Cys-Cy5 grafted onto RAFT-(cRGD)$_4$, before and after chemical cleavage of the disulfide bridge with 2-mercaptoethanol (2-MCE). A. Absorption spectrum and evolution thereof over time during the addition of 2-MCE. B. Demonstration that the addition of 2-MCE results in complete recovery of the absorption spectrum of Cy5. C. Evolution over time of the fluorescence of the imaging function during the addition of 2-MCE. D. Demonstration that the addition of 2-MCE results in complete recovery of the fluorescence of Cy5 (imaging function at 0.5 µM in 10 mM PBS, pH 7.2, [2-MCE]=85 mM).

FIG. 10 shows that the fluorescence of the Cy5 fluorophores is indeed initially self-quenched, and is completely released by chemical cleavage of the S—S disulfide bridge.

Synthesis of the Cysteine(Cy5)-S—S-Cysteine(QSY21) RAFTc[RGDfK-]$_4$ Molecular Probe FIG. 9 gives the structure of the cysteine(Cy5)-S—S-cysteine(QSY21)RAFTc[RGDfK-]$_4$ molecule. The cysteine-S—S-BoccyssteineRAFTc[RGDfK-]$_4$ peptide (19.9 mg, 4.45 μmol) is taken up in 0.4 ml of DMF with cyanines 5 N-hydroxysuccinimide (3.1 mg, 3.91 μmol). The solvent is removed under reduced pressure and the cysteine(Cy5)-S—S-BoccysteineRAFTc[RGDfK-]$_4$ peptide is taken up in 6 ml of 95/2.5/2.5 TFA/TIS/H$_2$O and purified by HPLC, and obtained in the form of a blue powder (11.5 mg, 51%). The cysteine(Cy5)-S—S-cysteineRAFTc[RGDfK-]$_4$ peptide is taken up in 300 μL of DMF with QSY21 N-hydroxysuccinimide (1.13 mg, 1.39 μmol) and purified by HPLC, and obtained in the form of a blue powder (1.2 mg, 20%).

Figure 11:
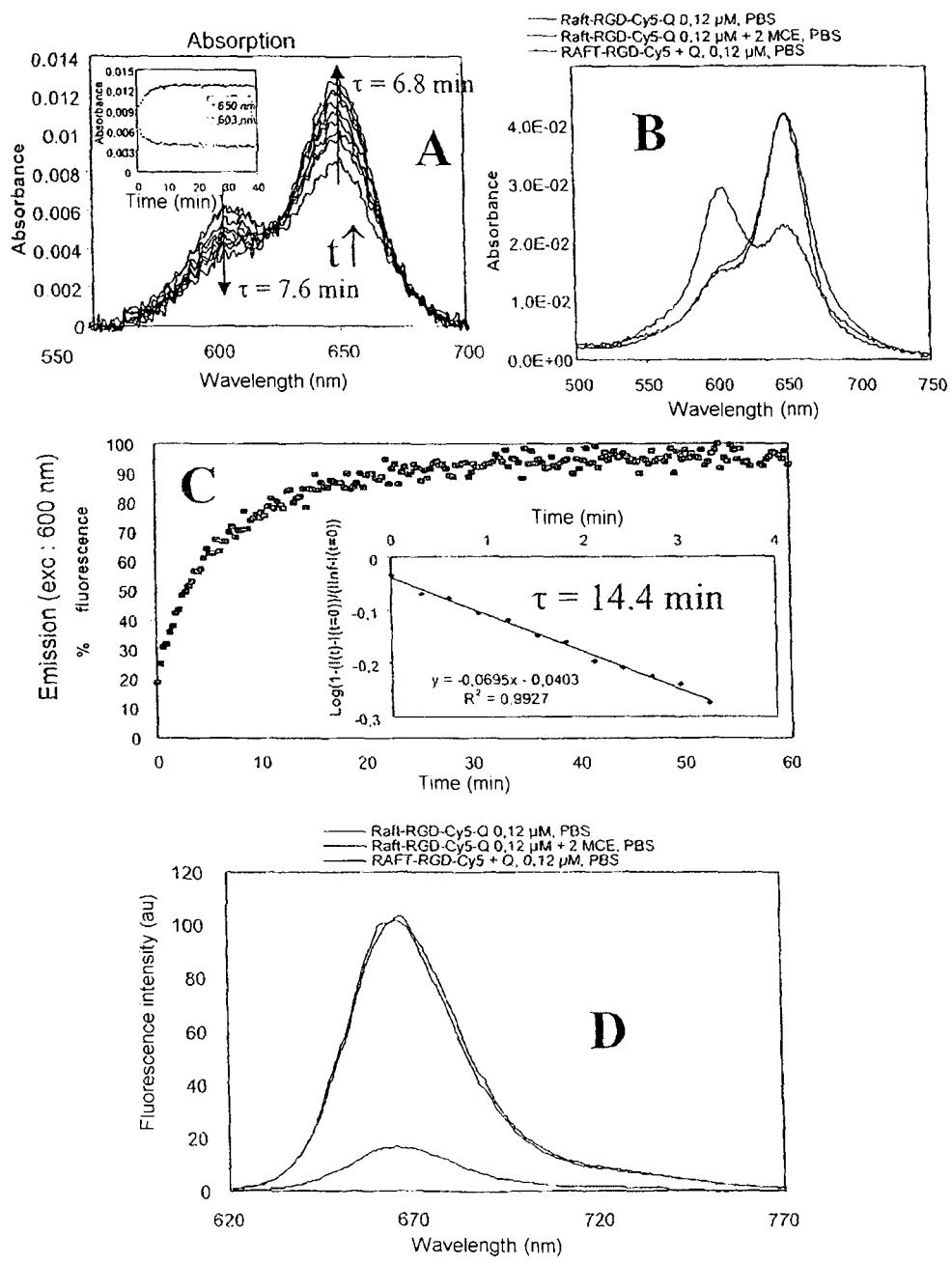
FIG. 11: Absorption and fluorescence of the imaging function Cy5-Cys-S—S-Cys-QSY21 grafted onto RAFT-(cRGD)$_4$, before and after chemical cleavage of the disulfide bridge with 2-mercaptoethanol (2-MCE). A. Absorption spectrum and evolution thereof over time during the addition of 2-MCE. B. Demonstration that the addition of 2-MCE results in complete recovery of the absorption spectrum of Cy5. C. Evolution over time of the fluorescence of the imaging function during the addition of 2-MCE. D. Demonstration that the addition of 2-MCE results in complete recovery of the fluorescence of Cy5 (imaging function at 0.10 µM in 10 mM PBS, pH 7.2, [2-MCE]=85 mM).

FIG. 11 shows that the fluorescence of the Cy5 fluorophore is clearly initially self-quenched, and is completely released by chemical cleavage of the S—S disulfide bridge.

Example 2

Optical Imaging of Tumors in the Nude Mouse

The molecular vectors RAFT-(cRGD)$_4$-Cy5-Cys-S—S-Cys-Cy5 and RAFT-(cRGD)$_4$-Cy5-Cys-S—S-Cys-QSY21 can be used for specifically imaging the endothelial cells of tumors overexpressing $\alpha_v\beta_3$ integrin receptors, such as IGROV-1 cells (human ovarian cancer model) implanted subcutaneously into a nude mouse.

The optical imaging is carried out by means of a commercially available or prototype fluorescence imaging device. The probes injected intravenously remain nonfluorescent in the animal's body outside the tumor (FIG. 8). After specific targeting of the tumors by the RGD ligand, the probes are internalized into the tumor cells. In the intracellular medium, the imaging functions are activated (FIG. 12). The subject of the invention therefore allows noninvasive optical imaging of tumors by means of a fluorescence imaging device, in vivo. It consequently makes it possible to follow the evolution of tumors over time or in response to a therapeutic treatment.

Biological Models and Injection of Labels

The mice used are female nude mice 6 to 8 weeks old, maintained under pathogen-free conditions. The IGROV-1 cells (human ovarian cancer model) are cultured in an RPMI 1640 culture medium containing 1% of glutamine, 10% of FCS, 50 U/ml of penicillin and 50 µg/ml of streptomycin. The cells are maintained at 37° C. under a humid atmosphere with 5% of $CO_2$. $10 \times 10^6$ cells are injected subcutaneously into the back of the mice 2 weeks before injection of the molecular vectors RAFT-(cRGD)$_4$-Cy5-Cys-S—S-Cys-Cy5 and RAFT-(cRGD)$_4$-Cy5-Cys-S—S-Cys-QSY21. The latter are injected into the tail intravenously, in 100 µl of PBS (pH 7.1, 9.5 mM), at doses of 10 nmol/mouse.

Fluorescence Reflectance Imaging Device

The anesthetized mice are imaged with a fluorescence reflectance imaging (FRI) device, comprising as excitation source a crown of LEDs equipped with interference filters, emitting at 633 nm (illumination power 50 µW·cm$^{-2}$). The images are collected after filtration with an RG665 colored filter of optical density>5 at the excitation wavelength by means of a CCD camera (Orca BTL, Hamamatsu), with an exposure time of 100 ms. The signals are quantified using image processing software.

Results Obtained

Figures 12A, 12B:
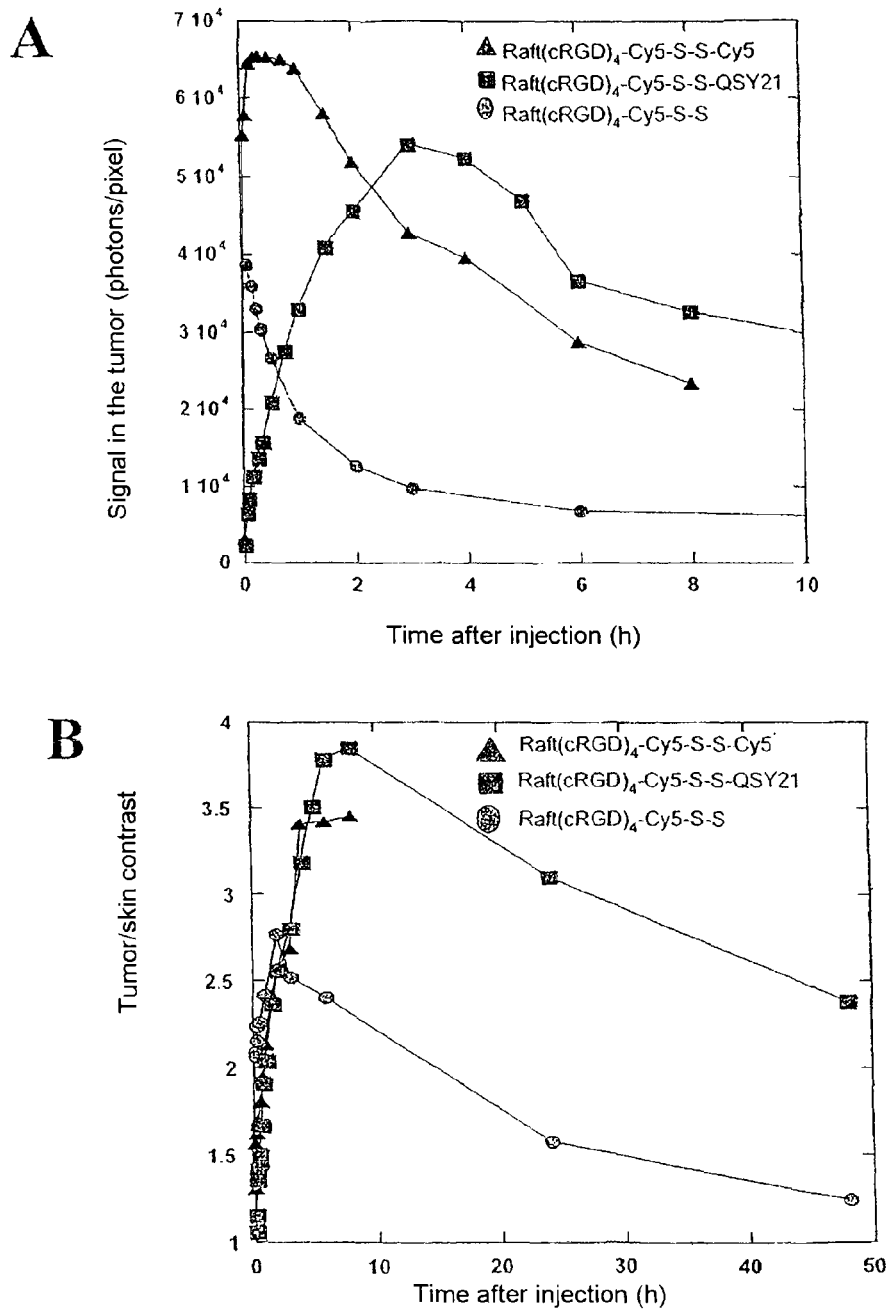
FIG. 12: Results of the in vivo injection of the molecular probes RAFT-(cRGD)$_4$-Cy5-Cys-S—S-Cys=Cy5, RAFT- (cRGD)$_4$-Cy5-Cys-S—S-Cys-QSY21, and RAFT-(cRGD)$_4$-Cy5-Cys-S—S-Cys (control) in nude mice, imaged using a fluorescence imaging device (excitation 633 nm; detection λ>670 nm). Intravenous injection of 10 nmol of probe/mouse, in 100 μL of PBS (pH 7.1, 9.5 mM), into the tail of anesthetized mice carrying, on the back, a subcutaneous tumor of IGROV-1 type (10 $10^6$ cells injected subcutaneously 2 weeks before imaging). A. Fluorescence intensity measured in the tumor over time. B. Ratio of the fluorescence intensities measured in the tumor and in the skin over time. C. Images obtained 10 minutes and 5 h after injection for the various molecular probes.
Figure 12C:

The results obtained are represented in FIG. 12. It appears that the activatable probes RAFT-(cRGD)$_4$-Cy5-Cys-S—S-Cys-Cy5 and RAFT-(cRGD)$_4$-Cy5-Cys-S—S-Cys-QSY21 produce more signal in the tumor than in the probe RAFT-(cRGD)$_4$-Cy5-Cys-S—S-cysteine, and bring about a gradual appearance of the signal in the tumor, as the probe is activated (and then its disappearance through elimination), whereas the probe RAFT-(cRGD)$_4$-Cy5-Cys-S—S-cysteine produces a signal which decreases very rapidly over time (FIG. 12A). Consequently, the contrast, i.e. the ratio of signal obtained between the tumor and the skin, increases when going from the probe RAFT-(cRGD)$_4$-Cy5-Cys-S—S-cysteine to the probes RAFT-(cRGD)$_4$-Cy5-Cys-S—S-Cys-Cy5 and RAFT-(cRGD)$_4$-Cy5-Cys-S—S-Cys-QSY21 (FIG. 12B).

The imaging functions described herein therefore clearly make it possible to obtain, due to the fact that the fluorescence of the probe is activated gradually and in a targeted manner in the tumors, a background noise that is lower in the rest of the animal's body than the corresponding targeted conventional probe.

Example 3

Comparison of the Imaging Functions
Cy5-Cys-S—S-Cys-Cy5 and Cy5-Cys-S—S-Cys-Q

Figure 13:
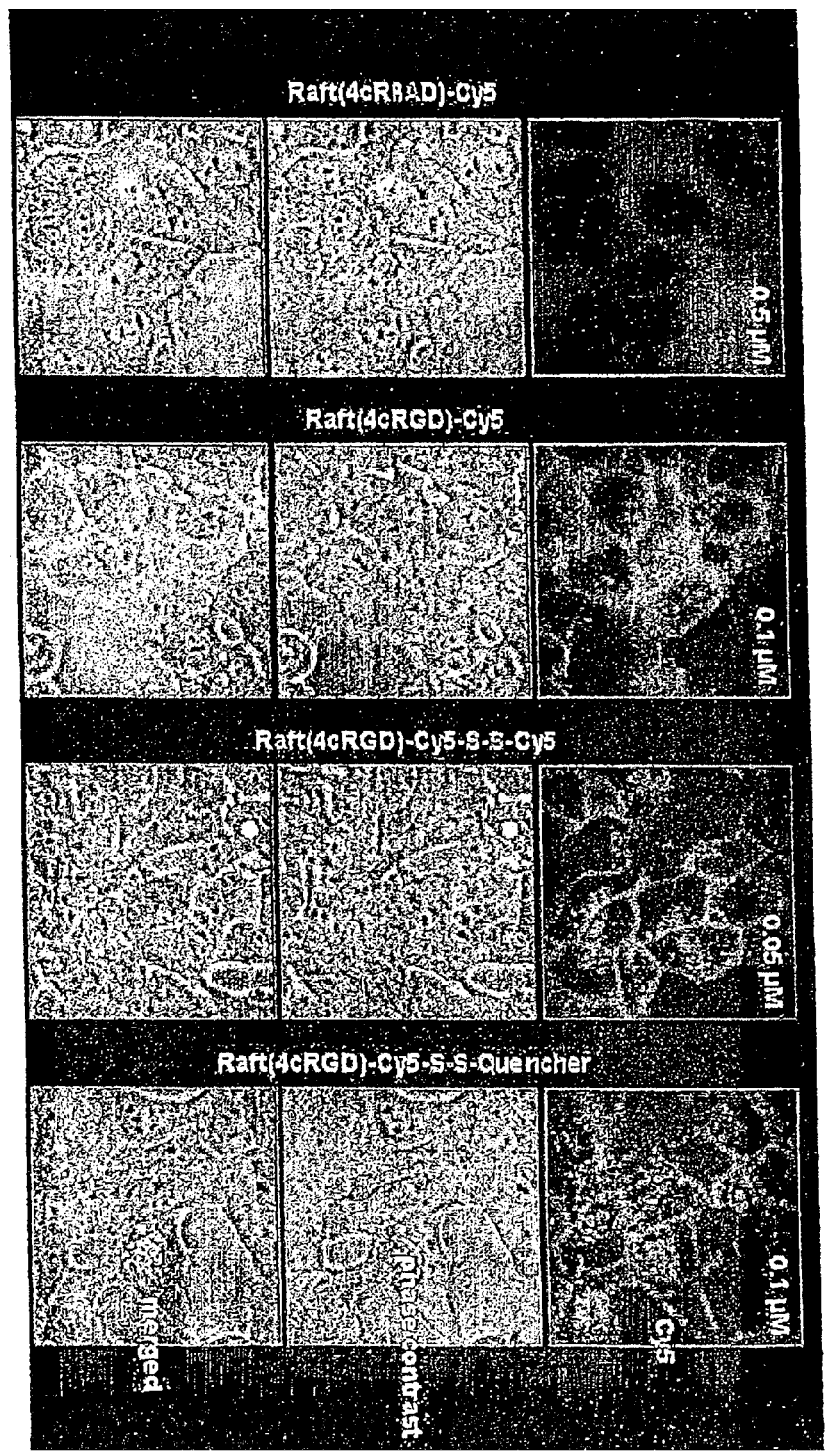
FIG. 13: Penetration of the labels into the cells, imaged by laser scanning confocal microscopy. Hekβ3 cells after 1 to 2 hours incubation in the presence of a negative control RAFT(4cRAD)-Cy5 (column 1), or in the presence of RAFT(4cRGD)-Cy5 (column 2), RAFT(4cRGD)-Cy5-Cys-S—S-Cys-Cy5 (column 3), or RAFT(4cRGD)-Cy5-Cys-S—S-Cys-quencher (column 4).

The penetration into the cells of the probes RAFT-(cRGD)$_4$-Cy5, RAFT-(cRGD)$_4$-Cy5-Cys-S—S-Cys-Cy5 and RAFT-(cRGD)$_4$-Cy5-Cys-S—S-Cys-QSY21 was observed on Hekβ3 cells, after 1 to 2 hours of incubation. The results, given in FIG. 13, show that, with the RAFT-(cRGD)$_4$-Cy5 probe, the fluorescence remains at the periphery of the cells (column 2); the cells incubated with RAFT-(cRGD)$_4$-Cy5-Cys-S—S-Cys-QSY21 show a clear fluorescence inside the cells (column 4), whereas, with the RAFT-(cRGD)$_4$-Cy5-Cys-S—S-Cys-Cy5 probe (column 3), a large amount of fluorescence is still visible at the level of the cell membrane, which proves that the probe does not enter well. These results illustrate the fact that a neutral molecule (in the case in point, RAFT-(cRGD)$_4$-Cy5-Cys-S—S-Cys-QSY21) penetrates into the cells better than a charged molecule.

The toxicity of the imaging functions Cy5-Cys-S—S-Cys-Cy5 and Cy5-Cys-S—S-Cys-Q was compared. 10 ml of solution of Cy5-Cys-S—S-Cys-Cy5 or of Cy5-Cys-S—S-Cys-Q (not grafted onto a vector), at approximately 0.5 µM in PBS, were incubated in the presence of TSA cells (approximately $20 \times 10^6$ cells/flask). Samples were taken from the solution at various time periods.

Figure 14:
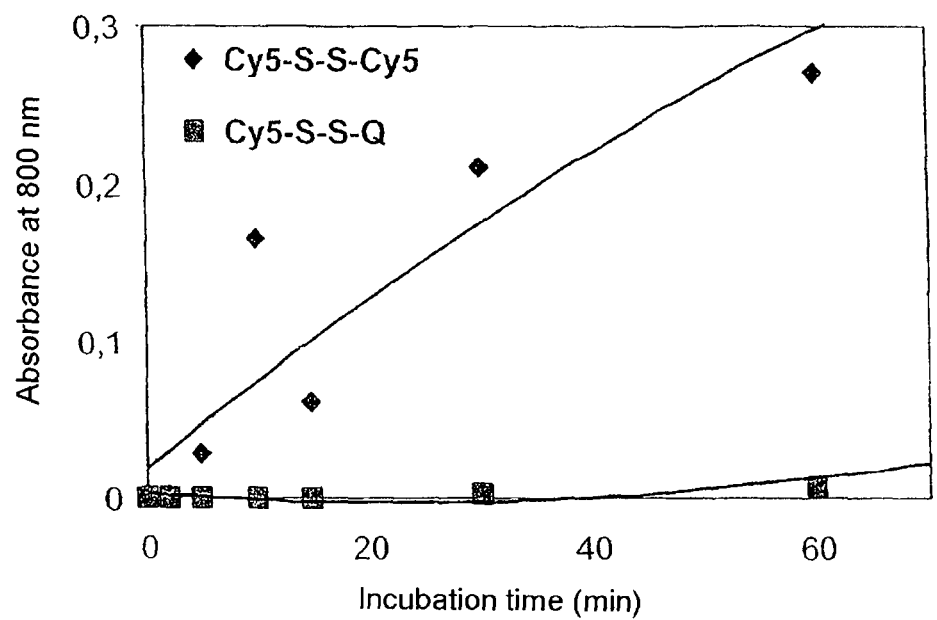
FIG. 14: Compared toxicity of the imaging functions Cy5-Cys-S—S-Cys-Cy5 and Cy5-Cys-S—S-Cys-Q. 10 ml of solution of Cy5-Cys-S—S-Cys-Cy5 or of Cy5-Cys-S—S-Cys-Q (not grafted to a vector), at approximately 0.5 μM in PBS, are incubated in the presence of TSA cells (approximately 20×$10^6$ cells/flask). Samples of this solution are taken at various time periods.

The results are given in FIG. 14. It is observed that, in the case of Cy5-Cys-S—S-Cys-Cy5, the solution becomes cloudy, which is reflected by considerable scattering by the solution, and therefore an increase in absorbance, in particular at 800 nm, a wavelength for which the Cy5, Cy5-Cys-S—S-Cys-Q and Cy5-Cys-S—S-Cys-Cy5 molecules do not normally absorb. This cloudiness of the solution, which means that it scatters light, is interpreted as being due to the fact that the cells have detached from the walls of the culture flask, indicating that they have been destroyed by Cy5-Cys-S—S-Cys-Cy5. In the case of the incubation in the presence of Cy5-Cys-S—S-Cys-Q, the cell death (and therefore the cell detachment) begins to exist only after 1 h of incubation and is to a much lesser degree. The Cy5-Cys-S—S-Cys-Cy5 molecule at 0.5 µM therefore causes cell death in the TSA cells, from the first minutes of incubation onward, unlike the Cy5-Cys-S—S-Cys-Q molecule.

REFERENCES

Arunachalam, B., U. Phan, et al. (2000). "Enzymatic reduction of disulfide bonds in lysosomes: characterization of a gamma-interferon-inducible lysosomal thiol reductase (GILT)." *Proceedings of the National Academy of Sciences, USA* 97 (2): 745-750.

Boturyn, D., J. L. Coll et al. (2004). "Template assembled cyclopeptides as multimeric system for integrin targeting and endocytosis." *J. Am. Chem. Soc.* 126 (18): 5730-5739.

Brooks, P. C., R. A. Clark et al. (1994). "Requirement of vascular integrin alpha v beta 3 for angiogenesis." *Science* 264: 569-571.

Curnis, F., G. Arrigoni, et al. (2002). "Differential binding of drugs containing the NGR motif to CD13 isoforms in tumor vessels, epithelia, and myeloid cells." *Cancer Res* 62 (3): 867-74.

Dumy, P., M. Favrot, et al. (2004). WO2004/026894, "Synthesis and characterization of novel systems for guidance and vectorization of molecules of therapeutic interest towards target cells."

Lakowicz, J. R. (1999). *Principles of Fluorescence Spectroscopy, 2nd edition.* New York, Kluwer Academics/Plenum Publishers.

The invention claimed is:

1. A targeted biological vector comprising:
   a Regioselectively Addressable Functionalized Template (RAFT) cyclodecapeptide vector core bound to:
   (i) at least one targeting molecule which is a peptide that comprises a RGD motif, and
   (ii) at least one activatable imaging function provided by a first fluorophore linked to a fluorescence quencher by an arm that is cleavable in an intracellular medium;
   wherein said arm comprises two adjacent cysteine residues bound by a disulfide bridge; and
   wherein said fluorophore is Cyanine 5 (Cy5), and said fluorescent quencher is QSY21.

2. The vector of claim 1, wherein said targeting molecule recognizes a receptor overexpressed on a surface of a cell.

3. The targeted biological vector of claim 1, wherein the targeting molecule is a ligand for a molecule over-expressed by a tumor cell or endothelial cell during neoangiogenesis.

4. The vector of claim 1, wherein said at least one targeting molecule is a cRGD cyclopeptide.

5. The vector of claim 1, wherein said at least one targeting molecule is an RGD peptide selected from the group consisting of cyclo(RGDfK), cyclo(RGDyK) and cyclo(RDGfV).

6. The vector of claim 1, wherein said at least one targeting molecule comprises an RGD peptide that recognizes an $\alpha_v\beta_3$ integrin that is expressed on the surface of a tumor cell.

7. The vector of claim 1, wherein said at least one targeting molecule comprises an RGD peptide that recognizes an $\alpha_v\beta_3$ integrin that is expressed on the surface of an endothelial cell during tumor neoangiogenesis.

8. The vector of claim 1, wherein said at least one targeting molecule comprises an RGD peptide selected from the group consisting of octeotrate peptide, a peptide analog of somatostatin, a peptide analog of bombesin, EGF (epidermal growth factor) or VIP (vasoactive intestinal peptide).

9. A vector comprising:
   a Regioselectively Addressable Functionalized Template (RAFT) cyclodecapeptide molecular vector bound to:
   (i) at least one targeting molecule which is a peptide that comprises a RGD motif, and
   (ii) an activatable imaging function comprising a fluorophore, a fluorescence quencher and an arm;
   wherein the fluorophore is Cyanine 5 (Cy5), and the fluorescence quencher is QSY21;
   wherein the fluorophore and fluorescence quencher are linked by said arm; and
   wherein said arm comprises two adjacent cysteine residues bound by a disulfide bridge and is cleavable in an intracellular medium.

10. The vector of claim 9, wherein said at least one targeting molecule is a cRGD cyclopeptide.

11. The vector of claim 9, wherein said at least one targeting molecule is an RGD peptide selected from the group consisting of cyclo(RGDfK), cyclo(RGDyK) and cyclo(RDGfV).

12. The vector of claim 9, wherein said at least one targeting molecule comprises an RGD peptide that recognizes an $\alpha_v\beta_3$ integrin that is expressed on the surface of a tumor cell.

13. The vector of claim 9, wherein said at least one targeting molecule comprises an RGD peptide that recognizes an $\alpha_v\beta_3$ integrin that is expressed on the surface of an endothelial cell during tumor neoangiogenesis.

14. The vector of claim 9, wherein said at least one targeting molecule comprises an RGD peptide selected from the group consisting of octeotrate peptide, a peptide analog of somatostatin, a peptide analog of bombesin, EGF (epidermal growth factor) or VIP (vasoactive intestinal peptide).

* * * * *